(12) United States Patent
Schmidt et al.

(10) Patent No.: US 7,881,764 B1
(45) Date of Patent: Feb. 1, 2011

(54) PHYSIOLOGICAL RECORDING DEVICE

(75) Inventors: Robert N. Schmidt, Cleveland, OH (US); Frederick J. Lisy, Euclid, OH (US); Gerard G. Skebe, Eastlake, OH (US); Troy S. Prince, Cleveland Heights, OH (US)

(73) Assignee: Orbital Reseach Inc., Cleveland, OH (US)

( * ) Notice: Subject to any disclaimer, the term of this patent is extended or adjusted under 35 U.S.C. 154(b) by 0 days.

(21) Appl. No.: 12/340,951

(22) Filed: Dec. 22, 2008

Related U.S. Application Data

(63) Continuation of application No. 11/906,234, filed on Oct. 1, 2007, now Pat. No. 7,489,959, which is a continuation of application No. 11/401,559, filed on Apr. 11, 2006, now Pat. No. 7,286,864, which is a continuation of application No. 10/874,075, filed on Jun. 22, 2004, now Pat. No. 7,032,301, which is a continuation of application No. 09/949,044, filed on Sep. 7, 2001, now Pat. No. 6,785,569.

(51) Int. Cl.
*A61B 5/04* (2006.01)
*H01R 43/00* (2006.01)

(52) U.S. Cl. ........................ 600/372; 600/373; 600/395; 29/825

(58) Field of Classification Search ................. 600/372, 600/373, 395
See application file for complete search history.

(56) References Cited

U.S. PATENT DOCUMENTS

| | | | | |
|---|---|---|---|---|
| 4,969,468 | A * | 11/1990 | Byers et al. | 600/373 |
| 6,117,077 | A * | 9/2000 | Del Mar et al. | 600/301 |
| 6,622,035 | B1 * | 9/2003 | Merilainen et al. | 600/391 |
| 6,782,283 | B2 * | 8/2004 | Schmidt et al. | 600/372 |

* cited by examiner

*Primary Examiner*—Lee S Cohen
(74) *Attorney, Agent, or Firm*—Brian M. Kolkowski; Robert Knecht Schmidt

(57) ABSTRACT

The present invention relates to a dry physiological recording electrode that can be used without skin preparation or the use of electrolytic gels. The dry physiological recording electrode comprising a substrate having an upper and a lower surface, and at least one penetrator(s) protruding from the upper surface of the substrate. The penetrator(s) is capable of piercing through the stratum corneum or outer layer of the skin, and transmitting an electric potential from the lower layers of the epidermis through the penetrator(s) which can be measured, or detecting agents from the lower layers of the epidermis primarily the stratum germinativum layer. At least one epidermis stop may be provided resulting in the formation of detritus troughs interposed between adjacent penetrator(s) and epidermis stops. The present invention also includes a method of sensing biopotentials in the skin.

14 Claims, 4 Drawing Sheets

PHYSIOLOGICAL RECORDING DEVICE

CROSS REFERENCE TO RELATED APPLICATIONS

This application is a continuation of U.S. patent application Ser. No. 11/906,234 filed on Oct. 1, 2007, which issued as U.S. Pat. No. 7,489,959 on Feb. 10, 2009 and which was a continuation of U.S. patent application Ser. No. 11/401,559 filed on Apr. 11, 2006, which issued as U.S. Pat. No. 7,286,864 on Oct. 23, 2007 and which was a continuation of U.S. patent application Ser. No. 10/874,075 filed on Jun. 22, 2004, which issued as U.S. Pat. No. 7,032,301 on Apr. 25, 2006 and which was a continuation of U.S. patent application Ser. No. 09/949,044 filed on Sep. 7, 2001, which issued as U.S. Pat. No. 6,785,569 on Aug. 31, 2004.

The U.S. Government has a paid-up license in this invention and the right in limited circumstances to require the patent owner to license others on reasonable terms provided for by the terms of grant number 1R43 NS37631-01 awarded by the National Institute of Neurological Disorder and Stroke of the National Institute of Health and grant number DMI-0109733 awarded by the National Science Foundation.

BACKGROUND OF THE INVENTION

1. Field of the Invention

The present invention is directed to a physiological recording electrode and, more particularly, to a physiological recording electrode that can be used without skin preparation or the use of electrolytic gels. The invention is further directed to penetrator with a size and shape which that will not bend or break, which limits the depth of application, and/or anchors the electrode or other device during normal application; and the use of stops which are integral with or separate from the penetrator that adjust the depth of application of the penetrator, and/or allows for uniform application of the electrode or other device over unprepared skin.

2. Technical Background

Electrodes for measuring biopotential are used extensively in modern clinical and biomedical applications. These applications encompass numerous physiological tests including electrocardiography (ECG), electroencephalography (EEG), electrical impedance tomography (EIT), electromyography (EMG) and electro-oculography (EOG). The electrodes for these types of physiological tests function as a transducer by transforming the electric potentials or biopotentials within the body into an electric voltage that can be measured by conventional measurement and recording devices.

In general, most commercial physiological electrodes for these applications today are placed on the surface of the skin. Because of this it is important to understand the anatomy of the skin to understand the problems encountered with these electrodes. The skin is a layered structure, which consists of the epidermis and the dermis. The dermis contains the vascular and nervous components. Further it is the part of the skin where pain has its origins. The epidermis is the most important layer in the electrode/skin interface. The epidermis consists of a number of layers as shown schematically in FIG. 1. These layers consist of:

a) Stratum basale or stratum germinativum, which contains living basal cells, that grow and divide, eventually migrating into the other layers of the epidermis;

b) Stratum spinosum, which contains living cells that have migrated from the stratum basale. The early stages of desmosomes can be found in this layer;

c) Stratum granulosum, which contains cells with many desmosomal connections, forms a waterproof barrier that prevents fluid loss from the body;

d) Stratum lucidum, which is a transition layer between the stratum granulosum and the stratum corneum. It is thickest in high friction areas such as the palms and the soles of the feet; and e) Stratum corneum, which is the outer layer, contains dry, dead cells, flattened to form a relatively continuous thin outer membrane of relatively continuous thin outer membrane of skin. The deeper cells of this layer still retain the desmosomal connections, but as they are pushed toward the surface by newly formed cells in the underlying layers, the junctions gradually break and the cells are lost.

The stratum corneum is the primary source of high electrical impedance. This is because dead tissue has different electrical characteristics from live tissue, and has much higher electrical impedance. Thus, this layer dramatically influences the biopotential measurements. The stratum corneum is estimated to be approximately one tenth the thickness of the epidermis except for the palms of the hand and the foot where this layer is much thicker. The stratum corneum, further, is very thin and uniform in most regions of the body surface ranging from 13-15 $\mu$m with a maximum of about 20 $\mu$m. If the high impedance results from the stratum corneum can be reduced, a more stable electrode will result. Therefore with existing physiological electrodes the skin must be prepared prior to application when lower impedance is required.

The most common electrode preparation methods to avoid the high impedance effects of the stratum corneum are: 1) shaving the hair from the skin; and either 2a) abrading the stratum corneum or 2b) using an electrolytic gel. The use of an electrolytic gel or fluid is often referred to as-"wet" electrodes. Hair is shaved from the skin to improve the contact between the electrodes and the skin surface. The goal of the abrasion of the stratum corneum is to reduce the thickness of (or remove) the stratum corneum (and therefore its electrically insulating characteristics). Drawbacks of abrading the skin are that the abraded area regenerates dead cells fairly quickly (resulting in a limited time period for using the electrode), and if the abrasion is too deep the person can experience pain. Additionally, electrolytic gels or fluids may be applied to abraded surface to enhance the contact. Alternatively, electrolytic gels or fluids can be applied to the surface of the skin directly. The electrolytic gel having a high concentration of conductive ions diffuses into the stratum corneum and improves its conductivity. Drawbacks observed with the use of electrolytic gels or fluids involve the change of conductivity with time as the gels dry, discomfort (an itching sensation) at the patients skin as a result of the gels drying, and the possibility of a rash due to an allergic reaction to the electrolytic gels.

Further drawbacks of "wet" electrodes include skin preparation and stabilization of the electrode with respect to the skin surface. This is because movement of the electrode on the surface of the skin causes the thickness of the electrolytic layer (formed by the electrolytic gels or fluids) to change resulting in false variation in the measured biopotential. Some electrode designs have an adhesive backing and/or grated surfaces to reduce the movement of the electrode on the skin surface, however, neither of these features eliminates completely the movement of the electrode with respect to the subject's skin. Another drawback is the length of time required to prepare the skin and apply the electrolytic gels or fluids prior to measurement of the biopotentials.

A less common type of physiological electrode is a non-polarizable "dry" electrode. These ceramic, high sodium ion conducting electrodes do not need an electrolytic gel before their application. The principal of the measurements from these physiological electrodes is based on a sodium ion exchange between the skin and the electrode. The skin-electrode impedance of these type of electrodes are found to decrease as a function of application time. This is a result of perspiration being produced by the body under the electrode almost immediately after application of the electrode on the skin. Drawbacks again, however, include many of those experienced with "wet" electrodes.

Another less common type of physiological electrode is an active "dry" electrode with an amplifier. Advances in solid-state electronic technology have made it possible to record surface biopotentials utilizing electrodes that can be applied directly to the skin without abrading the skin or using an electrolytic gel. These electrodes are not based on an electrochemical electrode-electrolyte interface. Rather, these electrodes are active and contain a very high impedance-converting amplifier. By incorporating the high impedance-converting amplifier into the electrode, biopotentials can be detected with minimal or no distortion. Although these electrodes offer the advantage of not requiring some of the preparation needed with conventional electrodes, they have certain inherent disadvantages. These electrodes are bulky in size due to the additional electronics and power sources required and they are typically more expensive to produce due to the electronic assembly required. Further, these electrodes also produce motion artifacts due to poor electrode-skin contact similar to electrodes requiring electrolytic gels or fluids.

In view of the foregoing inherent disadvantages with presently available wet and dry electrodes, it has become desirable to develop an electrode that does not require skin preparation or the use of electrolytic gels and overcomes the inherent disadvantages of presently available dry electrodes.

SUMMARY OF THE INVENTION

The present invention is directed to a physiological recording electrode and, more particularly, to a physiological recording electrode that can be used without skin preparation or the use of electrolytic gels. The invention is further directed to penetrator with a size and shape which that will not bend or break, which limits the depth of application, and/or anchors the electrode or other device during normal application; and the use of stops which are integral with or separate from the penetrator that adjust the depth of application of the penetrator, and/or allows for uniform application of the electrode or other device over unprepared skin.

In one embodiment, the present invention includes a dry physiological recording electrode comprising a substrate, and at least penetrator(s) which is formed from a conductive coating and is protruding from the substrate wherein the penetrator(s) is capable of piercing the stratum corneum or outer layer of the skin, and transmitting an electric potential from the lower layers of epidermis through the penetrator which can be measured.

In another embodiment, the present invention includes a dry physiological recording electrode comprising a thin metal sheet having an upper and a lower surface, and at least one penetrator(s) protruding from the upper surface of the thin metallic sheet wherein the penetrator(s) from the thin metal sheet are capable of piercing through the stratum corneum layer or outer layer of the skin and transmitting an electric potential from the lower layers of the epidermis through the penetrator(s) which can be measured.

In another embodiment, the present invention includes a dry physiological recording electrode comprising a silicon substrate having an upper and a lower surface, and at least one penetrator(s) protruding from the upper surface of the silicon substrate wherein the penetrator(s) has a side(s) and a slope for the side(s) which is substantially less than about 80 degrees along the side(s), and is capable of piercing through the stratum corneum or outer layer of the skin and transmitting an electric potential from the lower layers of the epidermis through the penetrator(s) which can be measured.

Additional features and advantages of the invention will be set forth in the detailed description which follows, and in part will be readily apparent to those skilled in the art from that description or recognized by practicing the invention as described herein, including the detailed description which follows, the claims, as well as the appended drawings.

It is to be understood that both the foregoing general description and the following detailed description are merely exemplary of the invention, and are intended to provide an overview or framework for understanding the nature and character of the invention as it is claimed. The accompanying drawings are included to provide a further understanding of the invention, and are incorporated in and constitute a part of this specification. The drawings illustrate various embodiments of the invention, and together with the description serve to explain the principles and operation of the invention.

DESCRIPTION OF THE PREFERRED EMBODIMENT

The present invention relates to a dry penetrating recording device and preferably a physiological recording electrode that does not require the use of electrolytic gels or any type of skin preparation. Traditionally, the monitoring of animal and in particular human physiological data has required that electrodes be attached to the skin with adhesive collars, tape or collodion after the skin has been vigorously cleaned to reduce the contact impedance. This approach is both time consuming and troublesome. With the advent of small portable physiologic recording devices, it has become possible to record data from individuals in-situ. It has also become feasible to conduct routine real-time monitoring of test subjects in a variety of environments. To fully exploit the capability of these portable physiological recording devices, an easy to use dry recording electrode similar to the present invention is required.

Figure 1:
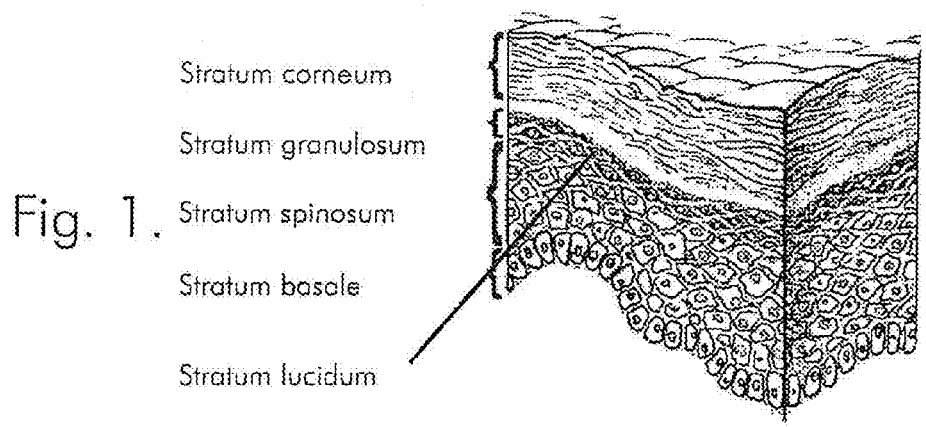
FIG. 1. Cross-sectional view of the epidermis layer of a person's skin.
Figure 2:
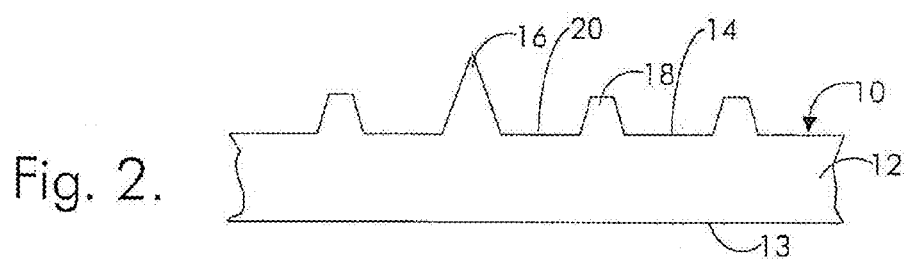
FIG. 2. Cross-sectional view of the dry physiological recording electrode of the present invention.

One embodiment of the present invention is shown in FIG. 2. This embodiment is a cross-sectional view of a portion of the dry physiological recording electrode 10. The dry physiological recording electrode 10 is comprised of a substrate 12 having an upper surface 14 and a lower surface 13. The upper surface 14 of the substrate 12 comprising at least one penetrator(s) 16 sized and shaped for piercing the stratum corneum or outer layer of the epidermis, and accessing the lower layers of the epidermis. The penetrator 16 can take many shapes including but not limited to pyramidal, needle-like, triangular, or any other shape that can be tapered to a point or tip.

Preferably, the size and shape of the penetrator 16 is such that the penetrator(s) 16 will not break or bend during normal use, will limit the depth the penetrator enters the skin under typical application conditions, and/or will anchor the electrode 10 to prevent motion artifacts or any substantial movement. Therefore, preferably, the appropriate aspect ratio of the height to the average width of the penetrator 16, slope of the edge(s) or side(s) of the penetrator 16, and/or height of the penetrator 16 are selected to make an electrode 10 wherein the penetrator(s) 16 will not break or bend, and will better anchor the electrode 10 during application. The height of the penetrator(s) is measured from the tip of the penetrator 16 perpendicular to the substrate 12. The penetrator(s) 16, preferably, has a height from about 20 to about 150 μm, and more preferably from about 40 to about 100 μm. The aspect ratio of the penetrator is ratio of the height divided by the average width of the penetrator. The average width of the penetrator 16 is measured by taking the widest average cross-section dimension of the cross-sections of the penetrator 16 perpendicular to the height. The penetrator(s) 16, preferably, has an aspect ratio of less than about 5, more preferably of less than about 2, even more preferably of less than about 1.5 and most preferably of less than about 0.75. The slope of the edge(s) or side(s) of the penetrator 16 is measured by drawing a line tangent to the edge or the side of the penetrator(s) at any given point to the substrate 12 and measuring the angle between the line and where it intersects the upper surface 14 of the substrate. While it is understood that the slope may or may not vary substantially along the edge or side of the penetrator(s), preferably the slope is less than about 80 degrees over substantially all of the edge or side of the penetrator 16, more preferably is less than about 70 degrees, and most preferably is less than about 60 degrees. By substantially all of the edge or side of the penetrator, it is meant that 60% of the length of the edge or side has a slope less than that set forth above. However, preferably, 75% of the length of the edge or side has a slope of less than that set forth and more preferably 90% of the length of the edge or side has a slope of less than that set forth. For this application, in the case of penetrator(s) 16 etched from thin sheets of material preferably a metal having a thickness of less than about 2 mm, the slope of the edge or side is always measured perpendicular to the thickness of the sheet metal.

Figure 3:
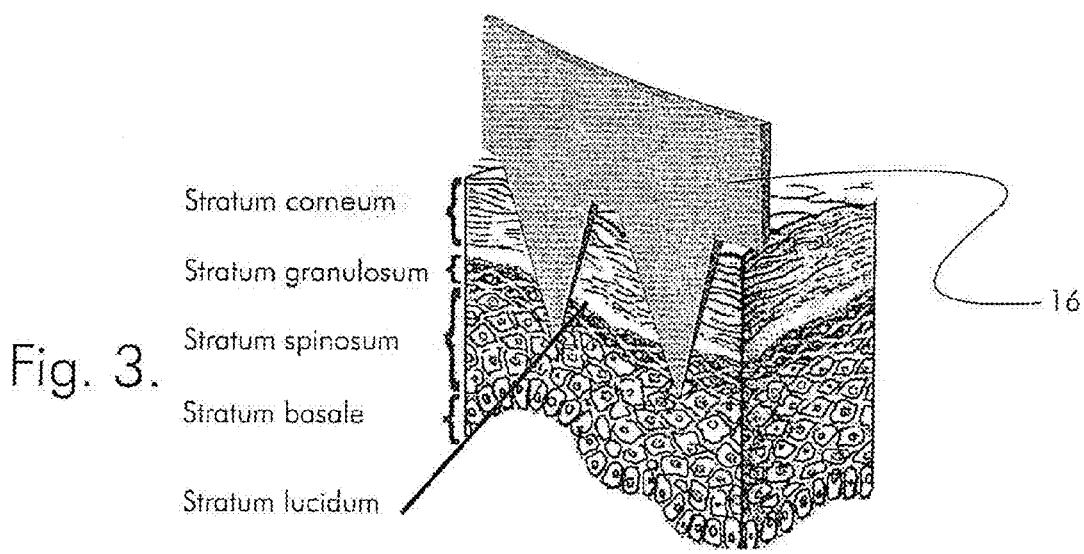
FIG. 3. Cross-sectional view of the epidermis layer and an illustration of the insertion of the penetrator(s) into the epidermis layer.

FIG. 3 is a schematic illustrating the insertion of the penetrator(s) into the epidermis. The penetrator(s) 16 are used to push through the high impedance upper layer or stratum corneum of the epidermis to reduce the contact impedance of the electrode. Preferably, the penetrator(s) 16 also "lock" the electrode into the chosen skin region and thus reduce motion artifacts. The penetrator(s) 16 are further used for physiological sensing in the lower layers of the epidermis. The lower layers of the epidermis include the other layers below the stratum corneum of the epidermis. Physiological sensing generally is the sensing of electric potentials. The penetrator(s) 16 are used transmit the electric potential from the lower layers of the skin, particularly the epidermis and more particularly the stratum germinativum layer of the epidermis. The electric potential then can be measured by conventional measuring devices.

Preferably, the surface of the penetrators 16 in contact with the skin for the dry physiological electrode 10 of the present invention are substantially non-chemically reactive with the chemicals in the skin and in particular the epidermis of the skin including NaCl, other chemicals and biological agents. By substantially non-chemically reactive it is meant that the majority of electric voltage (or potential) from the electrode isn't generated by the corrosion or through the deposition of materials on the surface of the penetrators 16 (similar to a chemical cell or battery). More preferably, less than about 30% of the electric voltage generated and transformed by the electrode is created by corrosion of the penetrators 16, even more preferably less than about 10%, and most preferably less than about 2%.

Epidermis stops 18 and detritus troughs 20 may also be provided on the upper surface 14 of the substrate 12. The detritus troughs 20 are the areas interposed between adjacent epidermis stops 18, adjacent penetrators 16 or adjacent epidermis stops 18 and penetrators 16. These troughs 20 when provided allow for a more accurate placement of the penetrator(s) 16 by allowing for displacement of the hair and other detritus on the skin in these troughs 20. Preferably, the detritus troughs 20 are sufficient in number and size to allow for placement of the electrode 10 on skin with a significant amount of hair such as for example the scalp or the chest of a male subject. Further preferably, the distance between the adjacent epidermis stops 18 and penetrator(s) 16 or adjacent penetrators 16 is at least 80 μm at their nearest points, more preferably at least 160 μm and most preferably at least 250 μm. Preferably, the shape of the penetrators 16 are such that they function as an epidermal stop by effectively limiting the depth of penetration of the penetrator 16 into the skin due to their shape and typical pressures and/or application techniques used when applying the packaged electrode 10 to the skin.

If provided, the epidermis stops 18 are of a particular height with respect to the height of the penetrator(s) 16 so as to prevent the penetrator(s) 16 from penetrating into the dermis of the skin where they might cause discomfort to the subject. In maximizing the area of the detritus troughs 20 that is available for optimal electrode to skin contact, while improving the probability that hair and other detritus will enter the troughs 20, the epidermis stops 18 preferably have a semi-circular shape in cross-section (not shown). The epidermis stops 18 may, however, have any shape know to those skilled in the art that would effectively prevent the penetrator(s) 16 from entering the dermis of the skin. Furthermore, the epidermis stops 18 are preferably applied in an array between each of the penetrator(s) 16, therefore further minimizing inadvertent deep penetration or over penetration by the penetrator(s).

Figure 5:
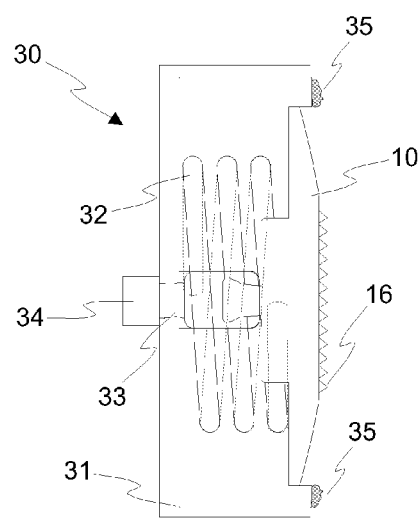
FIG. 5. Sectioned side schematic view of dry penetrating recording device.

Another embodiment of the present invention includes a dry penetrating recording device for measuring biological characteristics or biopotential (electric potential) from the lower layers of the epidermis. Shown in FIG. 5, this device comprises a substrate having an upper and a lower surface, at least one penetrator(s) 16 protruding from the upper surface of the substrate. Optionally, the device can further comprise at least one epidermal stop(s). The penetrator(s) and epidermal stop(s) for the device have similar characteristics such as size and shape to those described above for use with dry physiological electrodes.

The dry penetrating recording device 30 and the dry physiological electrode 10 of the present invention can be formed from a variety of processes and materials known to those skilled in the art. The substrate 12 from which the penetrators 16 are formed or to which they are added can by way of example but not limitation be made from the following: conductive metal sheet and conductive metals including for example stainless steel, nickel and copper; semi-conductive metal including for example silicon and doped silicon wafers; ceramics including for example oxides; and polymers including for example electrically insulating polymers such as polyimides. Preferably, all non-conductive substrates are coated or doped to make the substrate semi-conductive or conductive. There are however in general four processes by which embodiments of the present invention are preferably manufactured.

The first process is where the electrode 10 can be formed from metal sheet through photo micro-machining techniques. These techniques can be used to form the penetrator(s) 16 (and epidermis stops 18 and springs, if desired). With this process one edge of a thin gauge stock of metal, preferably stainless steel, is photo defined and chemically etched, effectively forming a thin cross section of a desired two dimensional surface containing at least one penetrator(s) 16 and, if desired, epidermis stops 18 and springs (not shown) on the lower surface. At this point various film layers, specific coatings and leads can be coated or deposited onto the electrode to make it individually addressable or to function as desired in an array. This forms an electrode 10 with a cross section with approximately the thickness of the thin gauge metal stock. Stainless steel is preferred because of its good biocompatibility, excellent corrosion resistance, and because of its ability to be cleaned and reused, however, a variety of other materials know in the art can also be used. An electrode array can be formed by stacking or laminating many of these thin strip electrodes 10 together. Additionally, laser machining, abrasion and other metal working techniques may be used to produce the electrode 10.

Figure 4:
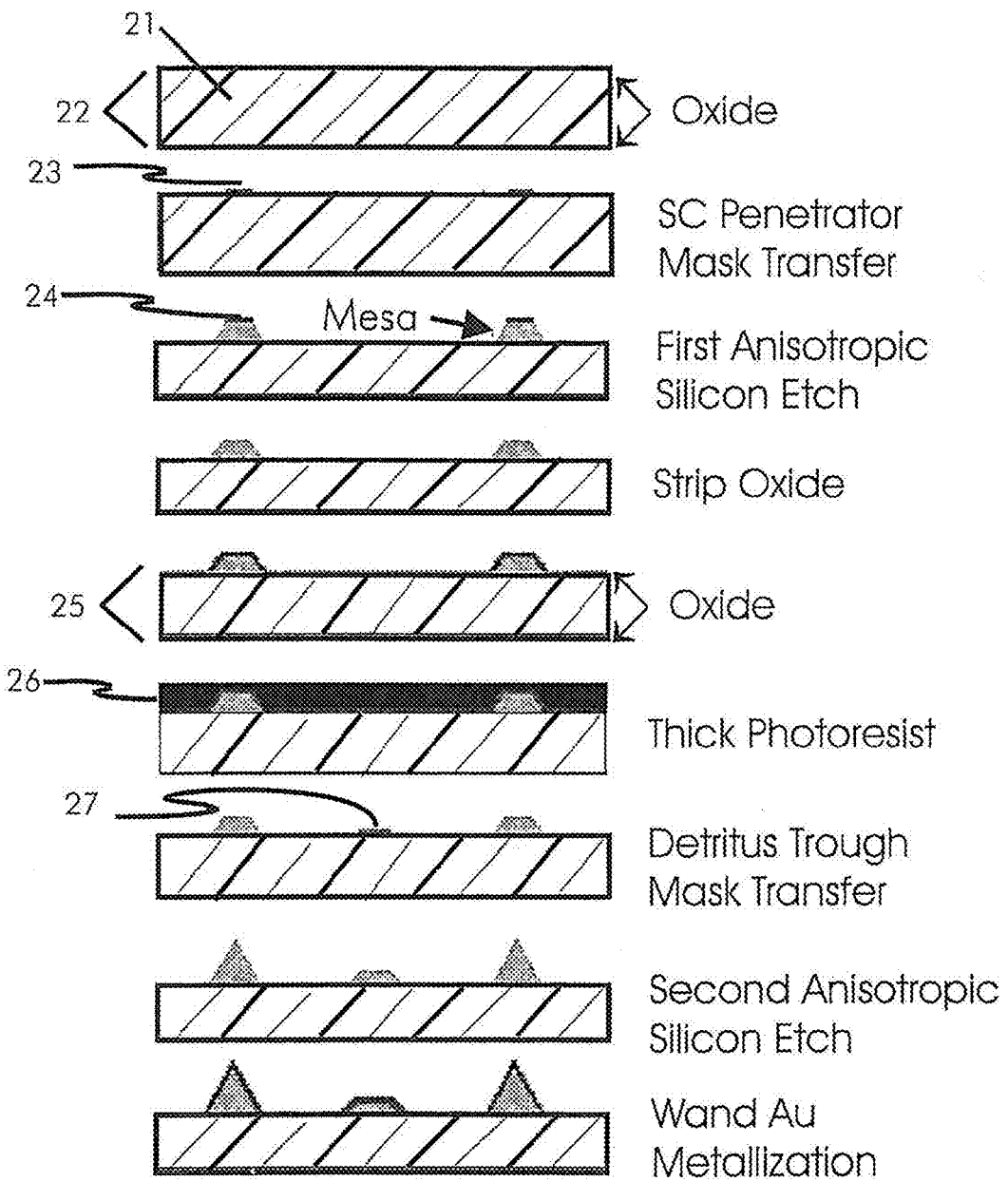
FIG. 4. Schematic of a process for micro-machining silicon electrodes.

For the second process the electrode 10 can be formed from silicon wafers, preferably (100) silicon wafers are used. FIG. 4 is a schematic showing the major process steps for silicon based micro machined dry electrode fabrication. In the first step of this process, an oxide layer 22 is formed on the silicon wafer 21. Following growth of the oxide layer 22, a photo resist (not shown) is applied and the pattern 23 for the major electrode peaks is transferred using a conventional photo resist process. Following application of the photo resist, the wafers 21 etched to form mesas 24 at what will ultimately become pyramidal electrode peaks. If epidermis stops 18 are not desired then further etching of the wafer 21 takes place to form the pyramidal electrode peaks. If, however, epidermis stops 18 are desired, following the anisotropic etch, the surface of the silicon wafer 21 is stripped of all oxides and masking material. Again, another oxide layer 25 is formed on the silicon wafer 21. Following the growth of the oxide layer 25, a fairly thick photo resist 26 is applied to the upper surface of the silicon wafer 21. Again, the photo resist is masked with a pattern 27 but this time for the epidermis stops. Then a second bulk anisotropic etch is used to form the epidermis stops and to finish the penetrator(s). After etching is completed, the remaining oxide is removed. At this point, the silicon optionally can be doped to increase the conductivity of the electrode, and also various film layers and leads can be coated onto the electrode to make it individually addressable or to function as desired in an array of electrodes 10.

With the third process the electrode 10 can be formed by an additive deposition process. Preferably, an electroplating process is used. Preferably, the substrate for this process is a flexible polymer, and more preferably an insulating polymer such as a polyimide. With this process a thin layer of metal is applied to the substrate. Then a thick layer of photo resist is applied to the thin layer of metal on the substrate and patterned by photolithography to create the desired features, i.e., arrays of squares, circles, etc. These patterns form the base of the electrodes and the other features of the electrode array. The photo resist is stripped from the substrate. Another layer of photoresist is applied. These patterns further define the penetrator structure which is built up to the desired height and shape by electroplating. Optionally, at this point various film layers and leads can be coated onto the electrode to make it individually addressable or to function to improve the conductivity as desired in an array of electrodes 10.

With the fourth process the electrode 10 may be formed by injection molding, casting or depositing a material into a mold. A mold with the imprint or negative image of the desired surface features which may include the penetrators, detritus troughs and epidermis stops is formed. This mold may be filled via injection molding, casting, deposition or other material forming technique to produce the desired electrode 10. Optionally and as a function of the conductivity of the material utilized, the surface may be doped to increase the conductivity of the electrode, and also various film layers and leads can be coated onto the electrode to make it individually addressable or to function as desired in an array of electrodes 10.

Figure 6A:
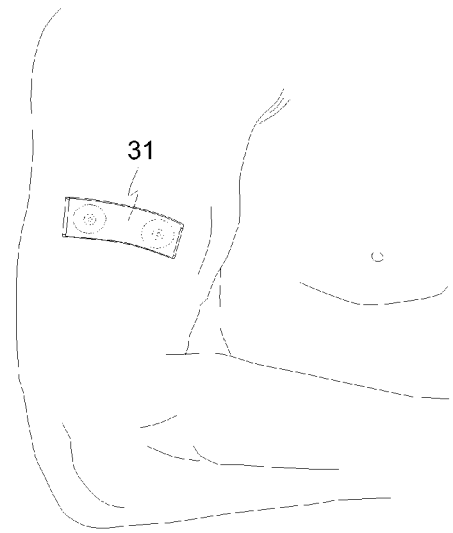
FIG. 6a. Illustration of dry penetrating recording device mounted to the skin using an adhesive.
Figure 6B:
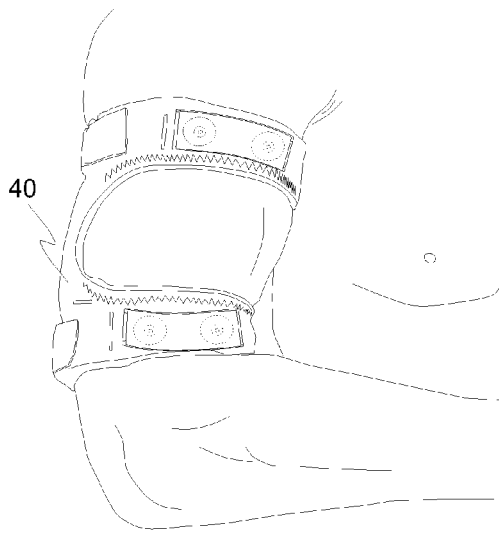
FIG. 6b. Illustration of dry penetrating recording device mounted to the skin using a harness.
Figure 6C:
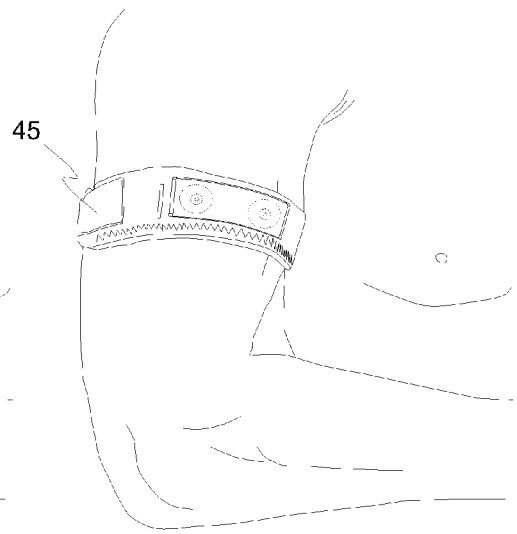
FIG. 6c. Illustration of dry penetrating recording device mounted to the skin using a band.

The electrodes of the present invention can be used in a variety of applications including but not limited to ECG, EEG, EIT, EMG, and EOG. The electrodes can be packaged by conventional packaging techniques, however, preferably the package 31 provides 1) adequate structural support for the electrode so it can be handled roughly (i.e., dropped, crushed, etc,) without damage; 2) a means (i.e., a spring 32, etc,) to force the electrode against the subject's skin with a consistent pressure; 3) a low impedance path 33 from the electrode's surface to the package's output connector 34; and 4) a design which allows for easy cleaning and sterilization for applications requiring reuse. These electrode packages also can be mounted to the skin using conventional techniques such as adhesives 35, harnesses 40 or bands 45, as shown in FIG. 6.

The dry physiological recording electrodes 10 are applied to an animal or human body having skin comprising an epidermis comprising a stratum corneum layer and lower layers of the epidermis, and a dermis. The penetrator(s) 16 of the electrode 10 pierce through the stratum corneum layer of the skin with the penetrator(s) such that the penetrator(s) does not enter the dermis of the skin. The penetrator(s) 16 senses the ionic current in the lower layers of the epidermis, and transforms a portion of the ionic current of the lower layers of the epidermis of the skin into an electric voltage through the penetrator(s) 16. The electric voltage from the penetrator(s) 16 is measured using conventional measuring devices.

Figure 7:
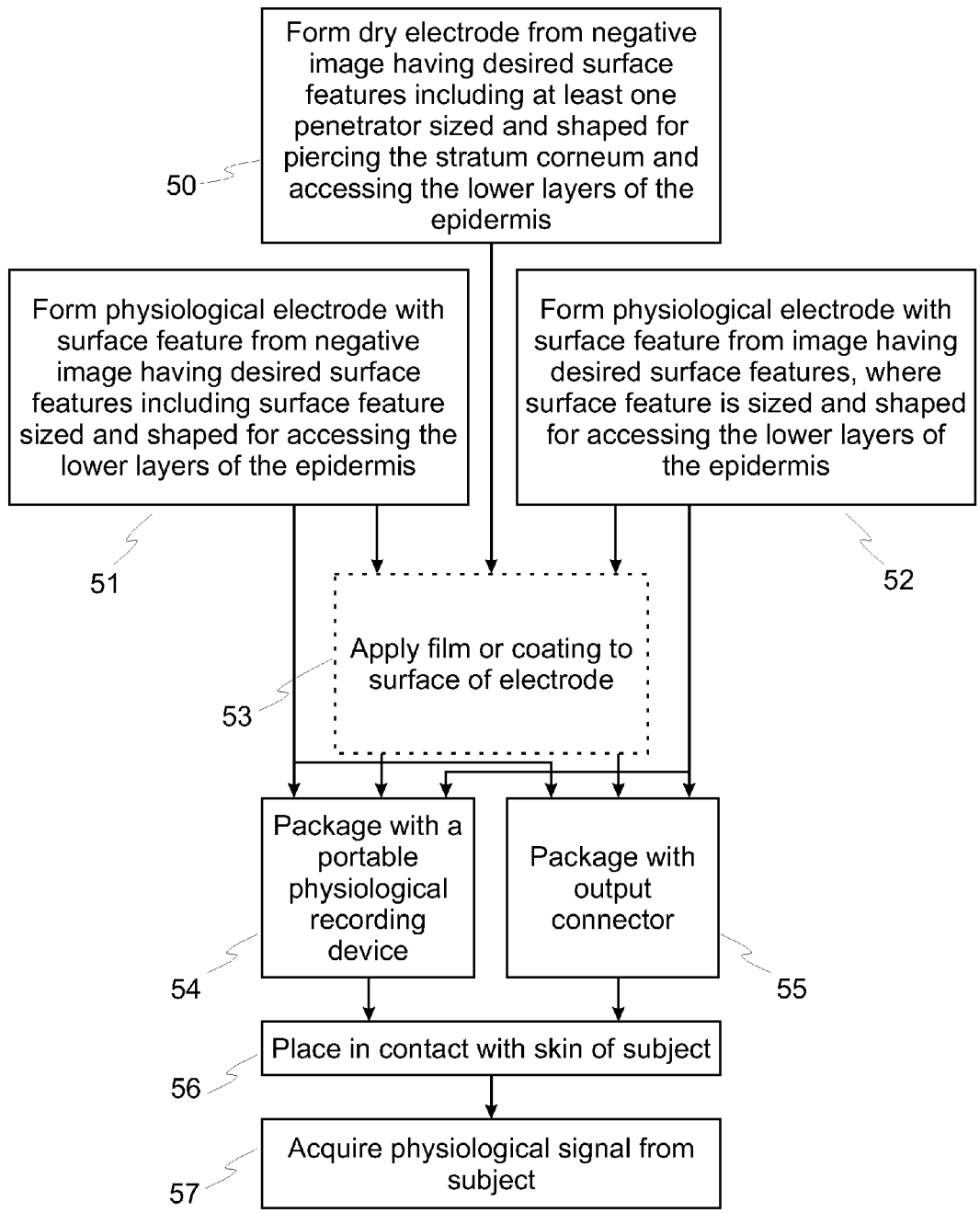
FIG. 7. Flow chart illustrating methods of use of physiological recording device.

FIG. 7 illustrates methods of acquiring physiological signals from a subject according to the present invention. In one embodiment, at least one dry electrode is formed 50 from a negative image having desired surface, where said surface features include at least one penetrator sized and shaped for piercing the stratum corneum or outer layer of the epidermis and accessing the lower layers of the epidermis. In another embodiment, a physiological electrode with at least one surface feature is formed 51 from an image having desired surface features, where the at least one surface feature is sized and shaped for accessing the lower layers of the epidermis. In yet another embodiment, at least one physiological electrode with at least one surface feature is formed 52 from an image having desired surface features, where the at least one surface feature is sized and shaped for accessing the lower layers of the epidermis. Preferably, the penetrator or surface feature has an aspect ratio of less than about 1.5. Further preferably, at least two penetrators or surface features are formed on the surface of the dry electrode, and they are individually addressable. Optionally, a film or coating may be applied 53 to the surface of the electrode before the electrode is packaged 54 with a portable physiological recording device or packaged 55 with an output connector. The packaged electrode is then placed 56 in contact with the skin of the subject, where it may be mounted with adhesives, harnesses, bands, or any other conventional techniques, and a physiological signal is thereby acquired from the subject 57. The physiological signal acquired may be, for example, ECG, EEG, EIT, EMG, or EOG.

It will be apparent to those skilled in the art that various modifications and variations can be made to the present invention without departing from the spirit and scope of the invention. Thus, it is intended that the present invention cover the modifications and variations of this invention provided they come within the scope of the appended claims and their equivalents.

What is claimed is:

1. A method of acquiring physiological signals from a subject having skin comprising
    forming at least one dry electrode from a negative image having desired surface features, where said surface features include at least one penetrator sized and shaped for piercing the stratum corneum or outer layer of the epidermis and accessing the lower layers of the epidermis,
    packaging the at least one dry electrode with a portable physiological recording device wherein the at least one dry electrode is capable of transmitting a signal to the recording device,
    placing the at least one dry electrode in contact with the skin of the subject, and
    acquiring a physiological signal from the subject.

2. The method of claim 1, wherein the at least one penetrator has an aspect ratio of less than about 1.5.

3. The method of claim 1, wherein the physiological signal acquired is ECG.

4. The method of claim 1, wherein at least two penetrators are formed on the surface of the dry electrode, and the at least two penetrators are individually addressable.

5. The method of claim 1, further including the step of applying a film or coating to the surface of the dry electrode.

6. A method of acquiring physiological signals from a subject having skin comprising
    forming a physiological electrode with at least one surface feature from an image having desired surface features, where the at least one surface feature is sized and shaped for accessing the lower layers of the epidermis,
    packaging the physiological electrode with a portable physiological recording device wherein the physiological electrode is capable of transmitting a signal to the portable physiological recording device,
    placing the physiological electrode in contact with the skin of the subject, and acquiring a physiological signal from the subject.

7. The method of claim 6, wherein the at least one surface feature has an aspect ratio of less than about 1.5.

8. The method of claim 6, wherein the physiological signal acquired is an ECG signal.

9. The method of claim 6, wherein at least two surface features are formed on the surface of the physiological electrode, and the at least two surface features are individually addressable.

10. The method of claim 6, further including the step of applying a film or coating to the surface of the dry electrode.

11. A method of acquiring physiological signals from a subject having skin comprising
    forming at least one physiological electrode with at least one surface feature from an image having desired surface features, where the at least one surface feature is sized and shaped for accessing the lower layers of the epidermis,
    packaging the at least one physiological electrode to provide a low impedance path from the electrode's surface to the package's output connector,
    placing the at least one physiological electrode in contact with the skin of the subject, and
    acquiring a physiological signal from the subject.

12. The method of claim 11, wherein the physiological signal acquired is an ECG signal.

13. The method of claim 11, wherein the package is mounted to the subject's skin with adhesives.

14. The method of claim 11, wherein at least two surface features are formed on the surface of the physiological electrode, and the at least two surface features are individually addressable.

* * * * *